United States Patent
Johansen (10) Patent No.: US 6,287,585 B1
(45) Date of Patent: Sep. 11, 2001

(54) METHODS FOR LAUNDRY USING POLYCATIONS AND ENZYMES

(75) Inventor: Charlotte Johansen, Holte (DK)

(73) Assignee: Novozymes A/S, Bagsvaerd (DK)

(*) Notice: Subject to any disclaimer, the term of this patent is extended or adjusted under 35 U.S.C. 154(b) by 0 days.

(21) Appl. No.: 09/143,622

(22) Filed: Aug. 28, 1998

Related U.S. Application Data (63) Continuation of application No. PCT/DK97/00098, filed on Mar. 5, 1997.

(30) Foreign Application Priority Data

Mar. 6, 1996 (DK) .................................................. 0262/96

(51) Int. Cl.$^7$ .......................... A01N 25/00; A01N 63/00; A01N 61/00; C11D 3/386; C11D 3/48
(52) U.S. Cl. ......................... 424/405; 510/276; 510/300; 510/360; 510/530
(58) Field of Search .................... 424/401, 405; 510/276, 530, 300, 360

(56) References Cited

U.S. PATENT DOCUMENTS

| | | | |
|---|---|---|---|
| 4,981,611 | * | 1/1991 | Kolattukudy et al. . |
| 5,082,585 | * | 1/1992 | Hessel et al. . |
| 5,356,803 | * | 10/1994 | Carpenter et al. . |
| 5,458,809 | * | 10/1995 | Fredj et al. . |
| 5,565,135 | * | 10/1996 | Dauderman et al. . |
| 5,677,384 | * | 10/1997 | Detering et al. . |

FOREIGN PATENT DOCUMENTS

| | | |
|---|---|---|
| 3 124 210 | * 12/1982 | (DE) . |
| 0 331 528 | 9/1989 | (EP) . |
| 61-47800 | * 3/1986 | (JP) . |
| 90/03732 | 4/1990 | (WO) . |
| 91/02459 | 3/1991 | (WO) . |
| 94/12607 | 6/1994 | (WO) . |
| 96/06532 | 3/1996 | (WO) . |

OTHER PUBLICATIONS

Novo–Nordisk AS (Research Disclosure 359044), Mar. 1994.*
STN International, File WPIDS, WPIDS, Accession No. 88–171767. (1988).
STN International, File WPIDS, WPIDS, Accession No. 90–053418. (1990).

* cited by examiner

Primary Examiner—Thurman K. Page
Assistant Examiner—Brian K. Seidleck
(74) Attorney, Agent, or Firm—Elias J. Lambiris; John I. Garbell

(57) ABSTRACT

The present invention provides a method of killing or inhibiting the growth of microbial cells present on laundry, comprising contacting the cells with a composition comprising a poly-cationic compound, preferably a polyamino acid, a polyvinylamine, a copolymer prepared from vinylamine and one or more carboxylic acid anhydrides, e.g. a polymer comprising 0.1–100 mol % vinyl amine or ethyleneimine units, 0–99.9 mol % units of at least one monomer selected from N-vinylcarboxamides of the formula I

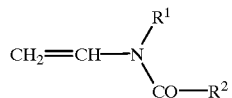

wherein $R^1$ and $R^2$ are hydrogen or $C_1$–$C_6$-alkyl;
vinyl formate, vinyl acetate, vinyl propionate, vinyl alcohol, $C_1$–$C_6$-alkyl vinyl ether, mono ethylenic unsaturated $C_3$–$C_8$-carboxylic acid, and esters, nitrites, amides and anhydrides thereof, N-vinylurea, N-imidazoles and N-vinyl imidazolines; and
0–5 mol % units of monomers having at least two unsaturated ethylenic double bonds;
and one or more enzymes, preferably glycanases, muranases, oxidoreductases, glucanases, proteases, amylases, lipases, pectinases and xylanases.

8 Claims, 2 Drawing Sheets

Figure 1

Figure 2

METHODS FOR LAUNDRY USING POLYCATIONS AND ENZYMES

CROSS-REFERENCE TO RELATED APPLICATIONS

This application is a continuation application of PCT/DK97/00098 filed Mar. 5, 1997 and claims priority under 35 U.S.C. 119 of Danish application 0262/96 filed Mar. 6, 1996, the contents of which are fully incorporated herein by reference.

The present invention relates to a method of killing or inhibiting microbial cells or microorganisms, more specifically microbial cells or microorganisms present in laundry, on hard surface, on skin, teeth or mucous membranes; and for preserving cosmetics etc.

BACKGROUND OF THE INVENTION

At this time of increased public interest in reducing the use of chemical additives, it is relevant to consider natural alternatives for antimicrobial agents used e.g. for preserving foods and cosmetics, as disinfectants, and as an antimicrobial ingredient of detergent and cleaning compositions. This has increased interest in preservation using live bacterial cultures (Jeppesen & Huss 1993) and enzymes like lactoperoxidase (Farrag & Marth 1992), glucose oxidase (Jeong et al. 1992) and lysozyme (Johansen et al. 1994).

Gram-negative bacteria are often resistant to a large number of harmful agents due to the effective permeability barrier function of the outer membrane (Nakae 1985). However, certain cationic peptides or polymers are under certain conditions apparently able to traverse the outer membrane of Gram-negative bacteria (Vaara 1992, Vaara & Vaara 1983), probably as a result of their binding to the anionic lipopolysaccharide-covered surface of the Gram-negative cell. The mechanism of the antibacterial action of basic peptides is not known, but it has been suggested that small or short cationic polymers can form a channel in the cytoplasmic membrane, thus uncoupling electron transport and causing leakage (Christensen et al. 1988; Hugo 1978; Kagan et al. 1990). It has also been proposed that they induce autolysis due to activation of the autolytic enzymes (Bierbaum & Sahl 1991). The larger or longer cationic basic polymers agglutinate the cells and may thereby inhibit growth.

Thus, the object of invention is co provide a method of killing or inhibiting microbial cells which is easy to use, relatively inexpensive, and more effective than the known disinfecting preserving methods.

SUMMARY OF THE INVENTION

Surprisingly, it has been found that the combined action of an enzyme and a cationic polymer, when applied to e.g. a hard surface, skin, mucous membranes or laundry, results in a hitherto unknown synergistic antimicrobial effect.

Thus, based on these findings the present invention provides, in a first aspect, a method of inhibiting microorganisms present in laundry, wherein the laundry is treated with a soaking, washing or rinsing liquor comprising a poly-cationic compound and one or more enzymes, with the proviso that when the enzyme is an oxidoreductase then the poly-cationic compound is not a polylysine, polyarginine or a co-polymer thereof.

In a second aspect, the present invention provides a method of inhibiting microbial growth on a hard surface, wherein the surface is contacted with a composition comprising a poly-cationic compound and one or more enzymes, with the proviso that when the enzyme is an oxidoreductase then the poly-cationic compound is not a polylysine, polyarginine or a co-polymer thereof.

In a third aspect, the present invention provides a method of killing microbial cells present on human or animal skin, mucous membranes, teeth, wounds, bruises or in the eye or inhibiting the growth thereof, wherein the cells to be killed or inhibited or the skin, mucous membrane, teeth, wound or bruise are/is contacted with a composition comprising a poly-cationic compound and one or more enzymes, with the proviso that when the enzyme is an oxidoreductase then the poly-cationic compound is not a polylysine, polyarginine or a co-polymer thereof.

The composition used in the methods of the invention is useful as antimicrobial ingredient wherever such an ingredient is needed, for example for the preservation of cosmetics, contact lens products, or enzyme compositions; as a disinfectant for use e.g. on human or animal skin, mucous membranes, wounds, bruises or in the eye; for killing microbial cells in laundry; and for incorporation in cleaning compositions or disinfectants for hard surface cleaning or disinfection.

DETAILED DESCRIPTION OF THE INVENTION

In the present context, the term "bactericidal" is to be understood as capable of killing bacterial cells.

In the present context, the term "bacteriostatic" is to be understood as capable of inhibiting bacterial growth, i.e. inhibiting growing bacterial cells.

In the present context, the term "fungicidal" is to be understood as capable of killing fungal cells.

In the present context, the term "fungistatic" is to be understood as capable of inhibiting fungal growth, i.e. inhibiting growing fungal cells.

The term "growing cell" is to be understood as a cell having access to a suitable nutrient and thus being capable of reproduction/propagation. By the term "non-growing cell" is meant a living, but dormant, cell, i.e. a cell in the non-growing, non-dividing, non-multiplying and non-energized state with metabolic processes at a minimum.

The term "microbial cells" denotes bacterial or fungal cells, and the term "microorganism" denotes a fungus, a bacterium and a yeast.

The term "hard surface" as used herein relates to any surface which is essentially non-permeable for microorganisms. Examples of hard surfaces are surfaces made from metal, plastics, rubber, board, glass, wood, paper, textile, concrete, rock, marble, gypsum and ceramic materials which optionally may be coated, e.g. with paint, enamel and the like.

The Enzyme

The term "oxidoreductase" means an enzyme classified as EC 1. according to the Enzyme Nomenclature (1992), i.e. any enzyme classified as EC 1.1 (acting on the CH—OH group of donors), EC 1.2 (acting on the aldehyde or oxo group of donors), EC 1.3 (acting on the CH—CH group of donors), EC 1.4 (acting on the CH—$NH_2$ group of donors), EC 1.5 (acting on the CH—NH group of donors), EC 1.6 (acting on NADH or NADPH), EC 1.7 (acting on other nitrogenous compounds as donors), EC 1.8 (acting on a sulfur group of donors), EC 1.9 (acting on a heme group of donors), EC 1.10 (acting on diphenols and related substances as donors), EC 1.11 (acting on a peroxide as acceptor), EC 1.12 (acting on hydrogen as donor), EC 1.13 (acting on single donors with incorporation of molecular oxygen (oxygenases), EQ 1.14 (acting on paired donors with incorporation of molecular oxygen), EC 1.15 (acting on superoxide radicals as acceptor), EC 1.16 (oxidizing metal ions), EC 1.17 (acting on —$CH_2$— groups), EC 1.18 (acting on reduced ferredoxin as donor), EC 1.19 (acting on reduced flavodoxin as donor), and EC 1.97 (other oxidoreductases).

The term "peroxidase enzyme system" is to be understood as a peroxidase (EC 1.11.1) in combination with a source of hydrogen peroxide which may be hydrogen peroxide or a hydrogen peroxide precursor for in situ production of hydrogen peroxide, e.g. percarbonate or perborate, or a hydrogen peroxide generating enzyme system, e.g. an oxidase and a substrate for the oxidase or an amino acid oxidase and a suitable amino acid, or a peroxycarboxylic acid or a salt thereof.

Examples of useful peroxidases are lactoperoxidase, horseradish peroxidase, peroxidases producible by cultivation of a peroxidase producing strain *Myxococcus virescens*, DSM 8593, *Myxococcus fulvus*, DSM 8969, or *Myxococcus xanthus*, DSM 8970, of a peroxidase producing strain of the genus Corallococcus, preferably belonging to *Corallococcus coralloides*, DSM 8967, or *Corallococcus exiguus*, DSM 8969.

Examples of useful substrates for peroxidase are thiocyanate, iodide, phenothiazins, syringates.

Laccases are enzymes that catalyze the oxidation of a substrate with oxygen, they are known from microbial, plant and animal origins. More specifically, laccases (EC 1.10.3.2) are oxidoreductases that function with molecular oxygen as electron acceptor. Molecular oxygen from the atmosphere will usually be present in sufficient quantity, so normally it is not necessary to add extra oxygen to the process medium. Examples of a laccase enzyme useful in the compositions of the present invention is laccase obtainable from the strain *Coprinus cinereus*, IFO 30116, or from a laccase having immunochemical properties identical to those of a laccase derived from *Coprinus cinereus*, IFO 30116; or obtainable from a strain of *Myceliophthora thermophila* as disclosed in WO 91/05839.

A useful proteolytic enzyme for the method of the present invention is any enzyme having proteolytic activity at the actual process conditions. Thus, the enzyme may be a proteolytic enzyme of plant origin, e.g. papain, bromelain, ficin, or of animal origin, e.g. trypsin and chymotrypsine, or of microbial origin, i.e. bacterial or fungal origin or from yeasts. It is co be understood that any mixture of various proteolytic enzyme may be applicable in the process of the invention.

In a preferred embodiment of the invention, the proteolytic enzyme is a serine-protease, a metallo-protease, or an aspartate-protease. A serine protease is an enzyme which catalyzes the hydrolysis of peptide bonds, and in which there is an essential serine residue at the active site. They are inhibited by diisopropylfluorophosphate, but in contrast to metalloproteases, are resistant to ethylene diamino tetraacetic acid (EDTA) (although they are stabilized at high temperatures by calcium ions). They hydrolyze simple terminal esters and are similar in activity to eukaryotic chymotrypsin, also a serine protease. A more narrow term, alkaline protease, covering a sub-group, reflects the high pH optimum of some of the serine proteases, from pH 9.0 to 11.0 The serine proteases usually exhibit maximum proteolytic activity in the alkaline pH range, whereas the metalloproteases and the aspartate-proteases usually exhibit maximum proteolytic activity in the neutral and the acidic pH range, respectively.

A sub-group of the serine proteases are commonly designated as subtilisins. A subtilisin is a serine protease produced by Gram-positive bacteria or fungi. The amino acid sequence of a number of subtilisins have been determined, including at least six subcilisins from Bacillus strains, namely, subtilisin 168, subtilisin BPN, subtilisin Carlsberg, subtilisin DY, subtilisin amylosacchariticus, and mesentericopeptidase, one subtilisin from an actinomycetales, thermitase from *Thermoactinomyces vulgaris*, and one fungal subtilisin, proteinase K from *Tritirachium album*. A further subgroup of the subtilisins, subtilases, have been recognised more recently. Subtilases are described as highly alkaline subtilisins and comprise enzymes such as subtilisin PB92 (MAXACAL®, Gist-Brocades NV), subtilisin 309(SAVINASE®, NOVO NORDISK A/S), and subtilisin 147 (ESPERASE®, NOVO NORDISK A/S).

In the context of this invention, a subtilisin variant or mutated subtilisin protease means a subtilisin that has been produced by an organism which is expressing a mutant gene derived from a parent microorganism which possessed an original or parent gene and which produced a corresponding parent enzyme, the parent gene having been mutated in order to produce the mutant gene from which said mutated subtilisin protease is produced when expressed in a suitable host.

These mentioned subtilisins and variants thereof constitute a preferred class of proteases which are useful in the method of the invention. An example of a useful subtilisin variant is a variant of subtilisin 309 (SAVINASE®) wherein, in position 195, glycine is substituted by phenylalanine (G195F or $^{195}$Gly to $^{195}$Phe).

Conveniently, conventional fermented commercial proteases are useful. Examples of such commercial proteases are Alcalase® (produced by submerged fermentation of a strain of *Bacillus licheniformis*), Esperase® (produced by submerged fermentation of an alkalophilic species of Bacillus), Rennilase® (produced by submerged fermentation of a non-pathogenic strain of *Mucor miehei*), Savinase® (produced by submerged fermentation of a genetically modified strain of Bacillus), e.g. the variants disclosed in the International Patent Application published as WO 92/19729, and Durazym® (a protein-engineered variant of Savinase®). All the mentioned commercial proteases are produced and sold by Novo Nordisk A/S, DK-2880 Bagsvaerd, Denmark. Other preferred serine-proteases are proteases from Nocardiopsis, Aspergillus, Rhizopus, *Bacillus alcalophilus, B. cereus, N. natto, B. vulgatus, B. mycoide,* and subtilins from Bacillus, especially proteases from the species Nocardiopsis sp. and *Nocardiopsis dassonvillei* such as those disclosed in the International Patent Application published as WO 88/03947, especially proteases from the species Nocardiopsis sp., NRRL 18262, and *Nocardiopsis dassonvillei*, NRRL 18133. Yet other preferred proteases are the serine proteases from mutants of Bacillus subtilins disclosed in the International Patent Application No. PCT/DK89/00002 and in the International Patent Application published as WO 91/00345, and the proteases disclosed in EP 415 296 A2.

Another preferred class of proteases are the metallo-proteases of microbial origin. Conveniently, conventional fermented commercial proteases are useful. Examples of such a commercial protease is Neutrase® (Zn) (produced by submerged fermentation of a strain of Bacillus subtilis), which is produced and sold by is Novo Nordisk A/S, DK-2880 Bagsvaerd, Denmark.

Other useful commercial protease enzyme preparation are Bactosol® WO and Bactosol® SI, available from Sandoz AG, Basle, Switzerland; Toyozyme®, available from Toyo Boseki Co. Ltd., Japan; and Proteinase K® (produced by submerged fermentation of a strain of Bacillus sp. KSM-K16), available from Kao Corporation Ltd., Japan.

Another enzyme which may be useful in the method of the present invention is a microbial lipase. As such, the lipase may be selected from yeast, e.g. Candida, lipases, bacterial, e.g. Pseudomonas or Bacillus, lipases; or fungal, e.g. Humicola or Rhizomucor, lipases. More specifically, suitable lioases may be the *Rhizomucor miehei* lipase (e.g. prepared as described in EP 238 023), *Thermomyces lanuginosa* lipase e.g. prepared as described in EP 305 216 (available from Novo Nordisk under the trade name Lipolase™), Humicola insolens lipase, *Pseudomonas stutzeri* lipase, *Pseudomonas cepacia* lipase, *Candida antarctica* lipase A or B, or lipases from rGPL, *Absidia blakesleena, Absidia corymifera, Fusarium solanil, Fusarium oxysporum, Penicillum cyclopium, Penicillum crustosum, Penicillum expansum, Rhodotorula glutinis, Thiarosporella phaseolina, Rhizopus microsporus, Sporobolomyces shibatanus, Aureobasidium pullulans, Fansenula anomala, Geotricum penicillaturn, Lactobacillus curvatus, Brochothrix thermosohata, Coprinus cinerius, Trichoderma harzanium, Trichoderma reesei, Rhizopus japonicus* or *Pseudomonas plantari*. Other examples of suitable lipases may be variants of any one of the lipases mentioned above, e.g. as described in WO 92/05249 or WO 93/11254.

Examples of amylases useful in the method of the present invention include Bacillus amylases, e.g. *Bacillus stearothermophilus* amylase, *Bacillus amyloliguefaciens* amylase, Bacillus subtilis amylase or *Bacillus licheniformis* amylase (e.g. as available from Novo Nordisk under the trade name Termamy®), or Aspergillus amylases, e.g. *Aspergillus niger* or *Aspergillus oryzae* amylase. Other examples of suitable amylases may be variants of any one of the amylases mentioned above, e.g. as described in U.S. Pat. No. 5,093, 257, EP 252 666, WO 91/00353, FR 2,676,456, EP 285 123, EP 525 610, PCT/DK93/00230.

Another useful enzyme is a "cellulase" or "cellulolytic enzyme" which refers to an enzyme which catalyses the degradation of cellulose to glucose, cellobiose, triose and other cello-oligosaccharides. Preferably, the cellulase is a 1,4-β-endoglucanase, more preferably a microbial endoglucanase, especially a bacterial or fungal endoglucanase. Examples of bacterial endoglucanases are endoglucanases derived from or producible by bacteria from the group of genera consisting of Pseudomonas or *Bacillus lautus*.

The cellulase or endoglucanase may be an acid, a neutral of an alkaline cellulase or endoglucanase, i.e. exhibiting maximum cellulolytic activity in the acid, neutral of alkaline range, respectively. Accordingly, a useful cellulase or endoglucanase is an acid cellulase or endoglucanase, preferably a fungal acid cellulase or endoglucanase, more preferably a fungal acid cellulase or endoglucanse enzyme with substantial cellulolytic activity at acidic conditions which is derived from or producible by fungi from the group of genera consisting of Trichoderma, Actinomyces, LMyrothecium, Aspergillus, and Botrytis.

A preferred useful acid cellulase or endoglucanase is derived from or producible by fungi from the group of species consisting of *Trichoderma viride, Trichoderma reesei, Trichoderma longibrachiatum, Myrothecium verrucaria, Aspergillus niger, Aspergillus oryzae,* and *Botrytis cinerea*.

Another useful cellulase or endoglucanase is a neutral or alkaline cellulase or endoglucanase, preferably a fungal neutral or alkaline cellulase or endoglucanase, more preferably a fungal alkaline cellulase or endoglucanase with substantial cellulolytlc activity at alkaline conditions which is derived from or producible by fungi from the group of genera consisting of Aspergillus, Penicillium, Myceliophthora, Humicola, Irpex, Fusarium, Stachybotrys, Scopulariopsis, Chaetomium, Mycogone, Verticillium, Myrothecium, Papulospora, Gliocladium, Cephalosporium and Acremonium, or as described in WO 96/29397.

A preferred alkaline cellulase or endoglucanase is derived from or producible by fungi from the group of species consisting of *Humicola insolens, Fusarium oxysporum, Myceliopthora thermophila,* or Cephalosporium sp., preferably from the group of species consisting of Humicola insolens, DSM 1800, *Fusarium oxysporum,* DSM 2672, *Myceliopthora thermophila,* CBS 117.65, or Cephalosporium sp., RYM-202, as described in WO 96/11262.

Examples of xylanases useful in the method of the present invention include enzymes having xylanolytic activity which are produced or producible by a strain selected from the group of species consisting of Humicola insolens (see e.g. WO 92/17573), Aspergillus aculeatus (an enzyme exhibiting xylanase activity, which enzyme is immunologically reactive with an antibody raised against a purified xylanase derived from *Aspergillus aculeatus,* CBS 101.43, see e.g. WO 94/21785), *Bacillus purnilus* (see e.g. WO 92/03540), *Bacillus stearathermophilus* (see e.g. WO 92/18976, WO 91/10724), Bacillus sp. AC13 (especially the strain NCIMB 40482, see e.g. WO 94/01532), *Trichoderma longibrachiatLrn* and Chainia sp. (see e.g. EP 0 353 342 A1), *Thermoascus aurantiacus* (see e.g. U.S. Pat. No. 4,966, 850), *Trichoderma harzianum* and *Trichoderma reseei* (see e.g. U.S. Pat. No. 4,725,544), *Aureobasidium pullulans* (see e.g. EP 0 373 107 A2), *Thermomyces lanuginosus* (see e.g. EP 0 456 033 A2), *Bacillus circulans* (WO 91/18978), *Aspergillus oryzae* (see e.g. SU 4610007), *Thermomonospora fusca* (see e.g. EP 0 473 545 A2), *Streptomyces lividans* (see e.g. WO 93/03155), *Streptomyces viridosporus* (see e.g. EP 496 671 A1), *Bacillus licheniformis* (see e.g. JP 9213868) and *Trichoderma longibrachiatum* [see W. J. J. van den Tweel et al.(Eds.), "Stability of Enzymes", Proceedings of an International Symposium heeld in Maastricht, The Netherlands, Nov. 22–25, 1992, Fisk, R. S. and Simpson, pp.323–328]; or from the group of genera consisting of Thermotoga (see e.g. WO 93/19171), Rhodothermus (see e.g. WO 93/08275), Dictyoglomus (see e.g. WO 92/18612) and Streptomyces (see e.g. U.S. Pat. No. 5,116,746). Other examples of suitable xylanases may be variants (derivatives or homologues) of any one of the above-mentioned enzymes having xylanolytic activty.

A useful pectinase may be an enzyme belonging to the enzyme classes polygalacturonases (EC3.2.1.15), pectinesterases (EC3.2.1.11), pectin lyases (EC4.2.2.10) and hemicellulases such as endo-1,3-b-xylosidase (EC 3.2.1.32), xylan 1,4-b-xylosidase (EC 3.2.1.37) and a-L-arabinofuranosidase (EC 3.2.1.55). A suitable source organism for pectinases may be Aspergillus niger.

Yet other useful enzymes are glucanases, cutinases, and muramidase (e.g. EC 3.2.1.92, peptidoglycan b-N-acetylmuramidase which catalyzes the hydrolysis of terminal, non-reducing N-acetylmuramic residues; and EC 3.2.1.17, lysozyme which catalyzes the hydrolysis of the 1,4-b-linkages between N-acetyl-D-glucosamine and N-acetylmuramic acid in peptisoglycan heteropolymers of the prokaryotes cell walls).

The enzymes to be used in the method of the invention may be monocomponent (recombinant) enzymes, i.e. enzymes essentially free from other proteins or enzyme proteins. A recombinant enzyme may be cloned and expressed according to standard techniques conventional to the skilled person. However, the enzyme may also be used in the form of an enzyme preparation optionally enriched in an enzyme exhibiting the desired enzyme activity as the major enzymatic component, e.g. a mono-component enzyme preparation.

The Polymer

In the present context, the term "poly-cationic compound" denotes a cationic polymer, i.e. a positively-charged polymer backbone.

In a preferred embodiment of the invention, the cationic polymer is a synthesized polymer, preferably a polymer prepared from cationic charged vinyl derivatives. Examples of useful vinyl derivatives are vinylamine, vinylcaprolactame, and vinylurea. Such cationic polymers can be copolymerized with other vinyl derivatives such as vinyl acetate, vinyl piperidon, methyl vinyl imidazol, methyl vinyl pyrrolidon, and vinyl formiate.

It is further contemplated that the following polymers are useful in the present invention: the copolymers disclosed in EP 0 331 528 (made from ethylene and dialkylaminoalkylacrylamides); copolymers made from N-vinylpyrrolidon and vinylamines and disclosed in Makromo. Chem., Suppl. Vol. 9, 25 (1985); polymers containing vinylphosphonium groups and vinylsulfonium groups disclosed in J. Polym. Sci., Part A: Polym. Chem., Vol. 31, 335, 1441, 1467, and 2873 (1993) and in Arch. Pharm. (Weinheim), 321, 89 (1988); and copolymers of diallyldimethylammoniumchloride and sodiumacrylate disclosed in SU 1071630, all of which are hereby incorporated by reference.

Examples of cationic polymers which are especially useful according to the present invention are polymers which comprise a) 0.1 to 100 mole vinyl amine or ethylene imine units,
b) 0 to 99.9 mol % units of at least one monomer selected from the group consisting of N-vinylcarboxyamides of the formula I wherein $R^1$ and $R^2$ are hydrogen or $C_1$–$C_6$-alkyl; vinyl formate, vinyl acetate, vinyl propionate, vinyl alcohol, $C_1$–$C_6$-alkyl vinyl ether, mono ethylenic unsaturated $C_1$–$C_8$-carboxylic acid, and esters, nitrites, amides and anhydrides thereof, N-vinylurea, N-imidazoles and N-vinyl imidazolines; and c) 0 to 5 mol % units of monomers having at least two unsaturated ethylenic double bonds, the total amount of a), b) and c) in the polymer always being 100 molt.

These polymers are well known from e.g. EP-B-0 071 050 and EP-B-0 216 387. The polymers containing vinyl amine units may e.g. be obtained by polymerization of a mixture so a) 0.1 to 100 mole of straight or branched N-vinylcarboxamides of the formula I,
b) 0 to 99.9 mol % units of at least one monomer selected from the group consisting of vinyl formate, vinyl acetate, vinyl propionate, $C_1$–$C_6$-alkylvinylether, monoethylenic unsaturated $C_3$–$C_8$-carboxylic acids, and esters, nitrils, amides and anhydrides thereof, N-imidazoles and N-vinylimidazolines; and c) 0 to 5 mol % units of monomers having at least two unsaturated ethylenic double bonds, followed by fully or partly cleaving of the group (II)

wherein $R^2$ has the meaning stated above for formula I, from the polymerized monomers of formula I.

Examples of straight or branched N-vinylcarboxamides of formula I are N-vinyl formamide, N-vinyl-N-methyl formamide, N-vinyl acetamide, N-vinyl-N-methyl acetamide, N-Vinyl-N-ethyl acetamide, N-vinyl-N-methyl propionamide and N-vinyl propionamide. The straight or branched vinyl-carboxamides may be used alone or in combination in the polymerization. A preferred monomer is N-vinyl formamide.

In the case of ethyleneimine-containing polymers is used polyethyleneimines which may be obtained by polymerization of ethyleneimine in the presence of acids, Lewis acids or acid-decomposing catalysts such as alkyl halides, e.g. methyl chloride, ethyl chloride, propyl chloride, methylene chloride, trichlormethane, carbon tetrachloride or carbon tetrabromide. The polyethyleneimines may have a molecular weight Mw in the range from 300 to 1,000,000. Other useful ethyleneimine-containing polymers are those obtainable by grafting of polyamidoamines with ethyleneimine or grafting of polymers of straight or branched N-vinyl carboxy amide having the above formula I with ethyleneimine. Grafted polyamidoamines are known from e.g. U.S. Pat. No. 4,144, 123.

The cationic polymers to be used according to the present invention comprises component (a) in an amount of from 0.1 to 100 mole, preferably from 10 to 90 mol %, of vinyl amine or ethyleneimine units. In case of ethyleneimine-containing polymers, it is preferred to use polyethyleneimine having a molecular weight of from 500 to 500,000.

Polymers containing vinyl amine units may be modified by copolymerizing the monomers of formula I with other monomers, e.g. with vinyl formate, vinyl acetate, vinyl propionate, $C_1$–$C_6$-alkylvinylether, monoethylenic unsaturated $C_3$–$C_8$ carboxylic acids, and esters, nitrils, amides and if possible also anhydrides thereof, N-vinyl urea, N-vinylimidazole and N-vinylimidazoline. Examples of monomers belonging to the mentioned group (b) are vinylesters of saturated carboxylic acids having 1–6 carbon atoms such as vinyl formate, vinyl acetate, vinyl propionate and vinylbutyrate, monoethylenic unsaturated $C_3$–$C_8$ carboxylic acids such as acrylic acid, methacrylic acid, dimethyl acrylic acid, ethacrylic acid, crotonic acid, vinyl acetic acid, allyl acetic acid, maleic acid, fumaric acid, citraconic acid and itaconic acid and esters, anhydrides, amides and nitriles thereof. Preferably useful anhydrides are e.g. maleic acid anhydride, citraconic acid anhydride, and itaconic acid anhydride.

Suitable esters which for example may be derived from alcohols with 1 to 6 C-atoms are methyl acrylate, methyl methacrylate, ethyl acrylate, ethyl methacrylate, isobutyl acrylate, hexyl acrylate or glycols or polyglycols, wherein only one OH-group of the glycols or polyglycols is esterified with a mono-ethylenic unsaturated carboxylic acid, e.g. hydroxyethyl acrylate, hydroxypropyl acrylate, hydroxypropyl methacrylate, hydroxybutyl acrylate and hydroxybutyl methacrylate. Other useful esters are acrylic acid monoesters and methacrylic acid monoesters of polyalkylene glycols having a molecular weight of below 10000, preferably from 1500 to 9000, and esters of the mentioned carboxylic acids with amino alcohols, e.g. dimethyl aminoethyl acrylate, dimethyl aminoethyl methacrylate, diethyl aminoethyl acrylate, diethyl aminoethyl methylacrylate, dimethyl aminopropyl acrylate, and dimethyl aminopropyl methacrylate. Suiable amides are for example acrylamide and methacrylamide. The basic acrylates can be added as a free base, as a salt with a mineral acid or a carboxylic acid, or also in a quaternary form. Other suitable comonomers are acrylonitrile, methacrylonitrile; N-vinylimidazol and substituted N-vinylimidazoles, e.g. N-vinyl-2-methylimidazole and N-vinyl-2-ethylimidazole; N-vinylimidazoline and substituted N-vinylimidazolines, e.g. N-vinyl-2-methylimidazoline. Further useful monoethylenic unsaturated monomers are monomers containing sulfonic groups, e.g. vinyl sulfonic acid, allyl sulfonic acid, styrol sulfonic acid, and acrylic acid-3-sulfonic propylester.

Preferably, the vinylamine-containing polymers contain:
a) 1–99 mol % of vinylamine units, and
b) 1–99 mol % units of monomers selected from the group consisting of N-vinylcarboxamides, vinyl formate, vinyl acetate, vinyl propionate, $C_1$–$C_6$-alkylvinylether, N-vinylurea, acrylic acid, methacrylic acid, maleic acid, and the anhydrides, esters, nitriles and amides of the mentioned carboxylic acids, N-vinylimidazole, N-vinylimidazoline and/or vinyl alcohol units,
wherein the total amount of a) and b) is 100 mol %.

The polymers containing vinylamine units may also be modified by using, in the copolymerization, such mixtures of monomers which contain as comonomer c) up to 5 mol % of a compound having at least two ethylenic unsaturated double bonds in the molecule. Thereby is obtained cross-linked copolymers which contain therein up to 5 mol % units of monomers with at least two ethylenic unsaturated double bonds in the molecule. If a cross-linking agent is used in the copolymerization, the preferred amount is 0.05–2 mol %. Use of monomers c) increases the molecular weight of the copolymers. Suitable monomer c) compounds are for example methylene-bis-acrylamide, esters of acrylic acid or methacrylic acid with polyvalent alcohols, e.g. glycoldimethacrylate or glycerintrimethacrylate, as well as polyols at least twice esterified with acrylic acid or methacrylic acid such as pentaerythrite and glucose. Further suitable cross-linking agents are divinylethylene urea, divinylbenzene, N,N'-divinyl urea, divinyldioxane, pentaerythrit triallylether, and pentaallylsucrose. From this group of compounds is preferably used watersoluble monomers, for example glycoldiacrylate or glycoldimethacrylate of polyethyleneglycols having a molecular weight not above 3000. The K-value of the copolymers is in the range from 5 to 300, preferably from 10 to 200. The K-values are determined according to H. Fikentscher in a 5% aqueous solution of NaCl at pH 7, 25° C., concentration of polymer: 0.5%.

The polymers containing vinylamine units are prepared according to known methods by polymerization of non-cyclic N-vinyl carboxamides of the formula I with
b) 0–99.9 mol % of at least one monomer selected from the group consisting of vinyl formate, vinyl acetate, vinyl propionate, $C_1$–$C_6$ alkyl vinylether, monoethylenic unsaturated $C_3$–$C_8$ carboxylic acids, and esters, nitrites, amides and anhydrides thereof, N-vinylimidazoles and N-vinylimidazolines; and
c) 0–5 mol % of at least one monomer having at least two ethylenic unsaturated double bonds,
in the presence or also in the absence of inert solvents or diluent. Then the —CO—$R^2$ group is eliminated in a polymer-analogue reaction in which vinylamine units are formed. Since the polymerization in the absence of inert solvents or diluents in most cases results in irregular polymers, the polymerization preferably takes place in an inert solvent or diluent. Suitable inert diluents are e.g. those in which the non-cyclic N-vinylcarboxamide is soluble. In case of solvent polymerization are suitable solvents inert solvents such as methanol, ethanol, isopropanol, n-propanol, n-butanol, sec.-butanol, tetrahydrofuran, dioxane, water as well as mixtures thereof. The polymerisation may be carried out continuously or batch-wise. It is carried out in the presence of radical-forming polymerization initiators which can be added e.g. in an amount of from 0.01 to 20, preferably from 0.05 to 10, weight % calculated on the basis of the monomers. The polymerization may also be initiated solely by using high-energy radiation, e.g. electronic radiation or UV-radiation.

In order to prepare polymers having a low K-value, e.g. from 5 to 50, preferably from 10 to 30, the polymerization is suitably carried out in the presence of a controlling agent. Suitable controlling agents are e.g. organic compounds containing sulphur in bonded form. Examples of such compounds are mercanto compounds, such as mercaptoethanol, mercaptopropanol, mercaptobutanol, mercapto acetic acid, mercapto propionic acid, butylmercaptane and dodecylmercaptane. Further useful controlling agents are allyl compounds such as allyl alcohol, aldehydes such as formaldehyde, acetaldehyde, propionaldehyde, n-butyraldehyde and isobutyraldehyde, formic acid, ammonium formate, propionic acid, hydrazinsulfate and butenole. If the polymerization is carried out in the presence of controlling agents, an amount of 0.05 to 20 weight %, calculated on basis of the monomers used for the polymerization, is to be used.

The polymerization of the monomers is usually carried out under an inert gas atmosphere, i.e. free of atmospheric oxygen. During the polymerization it is usually ensured that the reactants are thoroughly mixed. In the case of small-scale polymerization where it is important to ensure that the polymerization heat is removed, the monomers can be copolymerized discontinuously by heating the reaction mixture to the polymerization temperature followed by reacting mthe reactants. In this case the temperatures are in the range of 40–180° C., whereby it is possible to carry out the process under normal pressure, reduced pressure or increased pressure. Polymers having a high molecular weight are obtained when the polymerization is carried out in water. This may e.g. take place in the preparation of water-soluble polymers in aqueous solution, as a water-in-oil-emulsion or in accordance with the reverse suspension polymerization process.

In order to avoid saponification of the N-vinylcarboxyamide monomer during polymerization in aqueous solution, the polymerisation is preferably carried out at pH 4–9, preferably at a pH from 5 to 8. In many cases it is worthwhile to work in the presence of buffers, e.g. by adding primary or secondary sodium phosphate to the aqueous phase.

From the polymers described above is obtained, by cleavage of groups having the formula II from the monomeric units of the formula III, the vinylamine-containing polymers to be used according to the present invention under formation of amine or ammonium groups, respectively:

wherein $R^1$ and $R^2$ have the meaning as defined for formula I.

The hydrolysis is preferably carried out in the presence of water under the influence of acids, bases or enzymes, however, it can also be carried out in the absence of acids, bases or enzymes. Dependent on the reaction conditions for the hydrolysis, i.e. the amount of acid or base, calculated on basis of the polymer to be hydrolysed, and the reaction temperature of the hydrolysis, different degrees of hydrolysis are obtained. The hydrolysis is carried out to such an extent that 0.1–100 mol %, preferably 1–99 mol %, of the polymerized monomer units III are cleaved from the polymer. More preferably is used such polymers which contain 1–99 mol % of vinylamine units and 1–99 mole units having the formula III, preferably N-vinyl-Formamide units, wherein the total amount is always 100 mol %.

Acids which are suitable for the hydrolysis are e.g. mineral acids such as hydrogenhalides (gaseous or aqueous solution), sulphuric acid, HNO3, phosphoric acid (ortho-, meta- or polyphosphoric acid), and organic acids, e.g. caboxylic acids such as formic acid, acetic acid and propionic acid, or the aliphatic or aromatic sulfonic acids such as methanesulfonic acid, benzenesulfonic acid, or toluene-sulfonic acid. Preferably, hydrochloric acid or sulphuric acid is used for hydrolysis. The hydrolysis with acids is carried out at a pH of 0 and 5. For each formyl group equivalent in the polymer is required e.g. 0.05 to 1.5 equivalents of acid, preferably 0.4 to 1.2.

For the hydrolysis with bases may be used metal hydroxides of metals of the first and second main group of the periodic system, e.g. lithium hydroxide, sodium hydroxide, potassium hydroxide, calcium hydroxide, strontium hydroxide and barium hydroxide. However, ammonia and alkyl derivatives of ammonia may also be used, e.g. alkyl- or arylamines such as triethylamine, monoethanolamine, diethanolamine, triethanolamine, morpholine or aniline. In the hydrolysis with bases is pH in the range of 8 to 14. The bases may be used in solid, liquid or optionally also in gaseous form, either diluted or undiluted. Preferred bases to be used in the hydrolyses are ammonia, sodium hydroxide, or potassium hydroxide. The hydrolysis in the acidic or alkaline pH range is carried out at a temperature from 30° C. to 170° C., preferably from 50° C. to 120° C., prefereably for about 2 to 8 hours, preferably for 3 to 5 hours. In an especially preferred method of production, the bases or acids for the hydrolysis are added in aqueous solution. After the hydrolysis a.o. a neutralization is carried out in order Go obtain a pH of the hydrolyzed polymer solution in the range of 2 to 8, preferably in the range of 3 to 7. The neutralization is required in the case that further hydrolysis of partially hydrolyzed polymers is to be avoided or delayed. The hydrolysis can also be carried out by using enzymes.

For hydrolysis of copolymers of open-chained, i.e. non-cyclic, N-vinylcarboxamides of the formula I and at least one of the mentioned useful co-monomers, a further modification of the polymers takes place in that the polymerized co-monomers are also hydrolysed. In this way are obtained for example vinylalcohol units from polymerized vinylester units. Dependent on the conditions for hydrolysis, the polymerized vinylesters may be completely or partially hydrolyzed. In case of a partial hydrolysis of copolymers containing polymerized vinylacetate units, the hydrolyzed copolymer comprises, apart from the unaltered vinylacetate units, also vinylalcohol units as well as units of the formulas II and IV. By the hydrolysis of monoethylenic unsaturated carboxyanhydrides units is formed carboxylic acid units. Polymerized monoethylenic unsaturated carboxylic acids are chemically unchanged by the hydrolysis. In contrast thereto, ester and amide units are saponified with carboxylic acid units. From polymerized monoethylenic unsaturated nitrites is formed amide or carboxylic acid units, while vinylamine units are formed from polymerized N-vinyl urea. The degree of hydrolysis of the polymerized comonomers are readily determined by analysis.

Preferred polymers to be used according to the present invention contain polymerized units of
a) vinylamine, and
b) N-vinylformamide, vinylformate, vinylacetate, vinylpropionate, vinylalcohol, and/or N-vinylurea.

More preferred polymers comprise
a) 0.1–100 mol % of vinylamine units or ethyleneimin-units, and
b) 0–99.9 mol % of N-vinylformamide units.

These polymers are either fully or partially hydrolyzed homopolymers of vinylformamide or are polyethyleneimine. The partially hydrolyzed homopolymers of N-vinylformamide preferably comprise polymerized units of
a) 1–99 mol % of vinylamine, and
b) 1–99 mol % of N-vinylformamide
and have a K-value ranging from 5 to 300 (determined according to H. Fikentscher in 0.1 weight % of NaCl solution at 25° C. and a polymer concentration of 0.5 weights); more preferably the hydrolyzed homopolymers of the N-vinylformamides comprise polymerized units of
a) 10–90 mol % of vinylamine, and
b) 10–90 mol % of N-vinylformamide,
and have a K-value of 10 to 120 (determined according to H. Fikentscher in 0.1% NaC! solution at 25° C. and a polymer concentration of 0.5 weight %); the total amount of a) and b), calculated in mol %, always being 100.

Preferably, the copolymer contains at least 50% or vinylamine, calculated as the ratio of the total weight of vinylamine monomers to the total weight of the copolymer.

Preferably, the ratio of enzyme to cationic polymer is from 0.2 to 1000, more preferably from 5 to 200.

Preferably, the cationic polymer is present in the composition used in the method of the invention in an amount higher than 1 ppm.

The composition used in the method of the invention may be a detergent or cleaning composition comprising more enzyme types useful in detergent or cleaning compositions, preferably at least one further enzyme selected from the group consisting of proteases, amylases, cutinases, peroxidases, oxidases (e.g. laccases), cellulases, xylanases, and lipases.

Surfactant System

The detergent compositions useful in the method of the present invention comprise a surfactant system, wherein the surfactant can be selected from nonionic and/or anionic and/or cationic and/or ampholytic and/or zwitterionic and/or semi-polar surfactants.

The surfactant is typically present at a level from 0.1% to 60% by weight.

The surfactant is preferably formulated to be compatible with enzyme components present in the composition. In liquid or gel compositions the surfactant is most preferably formulated in such a way that it promotes, or at least does not degrade, the stability of any enzyme in these compositions.

Preferred systems useful in the method of the present invention comprise as a surfactant one or more of the nonionic and/or anionic surfactants described herein.

Polyethylene, polypropylene, and polybutylene oxide conden-sates of alkyl phenols are suitable for use as the nonionic surfactant of the surfactant, with the polyethylene oxide condensates being preferred. These compounds include the condensation products of alkyl phenols having an alkyl group containing from about 6 to about 14 carbon atoms, preferably from about 8 to about 14 carbon atoms, in either a straight chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available nonionic surfactants of this type include Igepal™ CO-630, marketed by the GAF Corporation; and Triton™ X-45, X-114, X-100 and X-102, all marketed by the Rohm & Haas Company. These surfactants are commonly referred to as alkylphenol alkoxylates (e.g., alkyl phenol ethoxylates).

The condensation products of primary and secondary aliphatic alcohols with about 1 to about 25 moles of ethylene oxide are suitable for use as the nonionic surfactant of the nonionic surfactant systems. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available nonionic surfactants of this type include Tergitol™ 15-S-9 (The condensation product of $C_{11}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-3 (the condensation product of $C_{12}$–$C_{13}$ linear alcohol with 3.0 moles of ethylene oxide), Neodol™ 45-7 (the condensation product of $C_{14}$–$C_{15}$ linear alcohol with 7 moles of ethylene oxide), Neodol™ 45-5 (the condensation product of $C_{14}$–$C_{15}$ linear alcohol with 5 moles of ethylene oxide) marketed by Shell Chemical Company, Kyro™ EOB (the condensation product of $C_{13}$–$C_{15}$ alcohol with 9 moles ethylene oxide), marketed by The Procter & Gamble Company, and Genapol LA 050 (the condensation product of $C_{12}$–$C_{14}$ alcohol with 5 moles of ethylene oxide) marketed by Hoechst. Preferred range of HLB in these products is from 8–11 and most preferred from 8–10.

Also useful as the nonionic surfactant of surfactant systems are alkylpolysaccharides disclosed in U.S. Pat. No. 4,565,647, having a hydrophobic group containing from about 6 to about 30 carbon atoms, preferably from about 10 to about 16 carbon atoms and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6-positions on the preceding saccharide units.

The preferred alkylpolyglycosides have the formula $$R^2O(C_nH_{2n}O)_t(\text{glycosyl})_x$$

wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, pre-ferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4-, and/or 6-position, preferably predominantly the 2-position.

The condensation products of ethylene oxide with a hydrophobic base formed by the condensation of propylene oxide with propylene glycol are also suitable for use as the additional nonionic surfactant. The hydrophobic portion of these compounds will preferably have a molecular weight from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic™ surfactants, marketed by BASF.

Also suitable for use as the nonionic surfactant of a nonionic surfactant system, are the condensation products of ethylene oxide with the product resulting from the reaction of propylene oxide and ethylenediamine. The hydrophobic moiety of these products consists of the reaction product of ethylenediamnine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic™ compounds, marketed by BASF.

Preferred for use as the nonionic surfactant of the surfactant systems are polyethylene oxide condensates of alkyl phenols, condensation products of primary and secondary aliphatic alcohols with from about 1 to about 25 moles of ethyleneoxide, alkylpolysaccharides, and mixtures hereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof.

Highly preferred nonionic surfactants are polyhydroxy fatty acid amide surfactants of the formula wherein $R^1$ is H, or $R^1$ is $C_{1-4}$ hydrocarbyl, 2-hydroxyethyl, 2-hydroxypropyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is straight $C_{11-15}$ alkyl or $C_{16-18}$ alkyl or alkenyl chain such as coconut alkyl or mixtures thereof, and Z is derived from a reducing sugar such as glucose, fructose, maltose or lactose, in a reductive amination reaction.

Highly preferred anionic surfactants include alkyl alkoxylated sulfate surfactants. Examples hereof are water soluble salts or acids of the formula $RO(A)_mSO3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydro-xyalkyl, more preferably $C_{12}$–$C_{18}$ alkyl or hydroxyalkyl, A is an ethoxy or propoxy unit, mL is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl, trimethyl-ammonium cations and Quaternary ammonium cations such as tetramethyl-ammonium and dimethyl piperdinium cations and those derived from alkylamines such as ethylamine, diethylamine, triethylamine, mixtures thereof, and the like. Exemplary surfactants are $C_{12}$–$C_{18}$ alkyl polyethoxylate (1.0) sulfate ($C_{12}$–$C_{18}$E(1.0)M), $C_{12}$–$C_{18}$ alkyl polyethoxylate (2.25) sulfate ($C_{12}$–$C_{18}$ (2.25)M, and $C_{12}$–$C_{18}$ alkyl polyethoxylate (3.0) sulfate ($C_{12}$–$C_{18}$E(3.0) M), and $C_{12}$–$C_{18}$ alkyl polyethoxylate (4.0) sulfate ($C_{12}$–$C_{18}$E(4.0) M), wherein M is conveniently selected from sodium and potassium.

Suitable anionic surfactants to be used are alkyl ester sulfonate surfactants including linear esters of $C_8$–$C_{20}$ carboxylic acids (i.e., fatty acids) which are sulfonated with gaseous $SO_3$ according to "The Journal of the American Oil Chemists Society", 52 (1975), pp. 323–329. Suitable starting materials would include natural fatty substances as derived from tallow, palm oil, etc.

The preferred alkyl ester sulfonate surfactant, especially for laundry applications, comprise alkyl ester sulfonate surfactants of the structural formula:

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation which forms a water soluble salt with the alkyl ester sulfonate.

Suitable salt-forming cations include metals such as sodium, potassium, and lithium, and substituted or unsubstituted ammonium cations, such as monoethanolamine, diethonolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{10}$–$C_{16}$ alkyl.

Other suitable anionic surfactants include the alkyl sulfate surfactants which are water soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperdinium cations and quaternary ammonium cations derived from alkylamines such as ethylamine, diethylamine, triethylamine, and mixtures thereof, and the like). Typically, alkyl chains of $C_{12}$–$C_{16}$ are preferred for lower wash temperatures (e.g. below about 50° C.) and $C_{16}$–$C_{18}$ alkyl chains are preferred for higher wash temperatures (e.g. above about 50° C.).

Other anionic surfactants useful for detersive purposes can also be included in the laundry detergent compositions useful in the method of the present invention. Theses can include salts (including, for example, sodium, potassium, ammonium, and substituted ammonium salts such as mono- di- and triethanolamine salts) of soap, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{18}$ monoesters) and diesters of sulfosuccinates (especially saturated and unsaturated $C_6$–$C_{12}$ diesters), acyl sarcosinates, sulfates of alkylpolysaccharides such as the sulfates of alkylpolyglucoside (the nonionic nonsulfated compounds being described below), branched primary alkyl sulfates, and alkyl polyethoxy carboxylates such as those of the Formula $RO(CH_2CH_2O)_k$—$CH_2COO$—M+ wherein R is a $C_8$–$C_{22}$ alkyl, k is an integer from 1 to 10, and M is a soluble salt forming cation. Resin acids and hydrogenated resin acids are also suitable, such as rosin, hydrogenated rosin, and resin acids and hydrogenated resin acids present in or derived from tall oil.

Alkylbenzene sulfonates are highly preferred. Especially preferred are linear (straight-chain) alkyl benzene sulfonates (LAS) wherein the alkyl group preferably contains from 10 to 18 carbon atoms.

Further examples are described in "Surface Active Agents and Detergents" (Vol. I and II by Schwartz, Perrry and Berch). A variety of such surfactants are also generally disclosed in U.S. Pat. No. 3,929,678, (Column 23, line 58 through Column 29, line 23, herein incorporated by reference).

When included therein, laundry detergent compositions typically comprise from about 1 to about 40%, preferably from about 3% to about 20% by weight of such anionic surfactants.

Laundry detergent compositions may also contain cationic, ampholytic, zwitterionic, and semi-polar surfactants, as well as the nonionic and/or anionic surfactants other than those already described herein.

Cationic detersive surfactants suitable for use in laundry detergents are those having one long-chain hydrocarbyl group. Examples of such cationic surfactants include the ammonium surfactants such as alkyltrimethylammonium halogenides, and those surfactants having the formula:

wherein $R^2$ is an alkyl or alkyl benzyl group having from about 8 to about 18 carbon atoms in the alkyl chain, each $R^3$ is selected norm the group consisting of $-CH_2CH_2-$, $-CH_2CH(CH_3)-$, $-CH_2CH(CH_2OH)-$, $-CH_2CH_2CH_2-$, and mixtures thereof; each $R^4$ is selected from the group consisting of $C_1-C_4$ alkyl, $C_1-C_4$ hydroxyalkyl, benzyl ring structures formed by joining the two $R^4$ groups, $-CH_2CHOHCHOHCOR^6CHOHCH_2OH$, wherein $R^6$ is any hexose or hexose polymer having a molecular weight less than about 1000, and hydrogen when y is not 0; $R^5$ is the same as $R^4$ or is an alkyl chain, wherein the total number of carbon atoms or $R^2$ plus $R^5$ is not more than about 18; each y is from 0 to about 10, and the sum of the y values is from 0 to about 15; and X is any compatible anion.

Highly preferred cationic surfactants are the water soluble quaternary ammonium compounds useful in the present composition having the formula:

$$R_1R_2R_3R_4N^+X^- \qquad (i)$$

wherein $R_1$ is $C_8-C_{16}$ alkyl, each of $R_2$, $R_3$ and $R_4$ is independently $C_1-C_4$ alkyl, $C_1-C_4$ hydroxy alkyl, benzyl, and $-(C_2H_{40})_xH$ where x has a value from 2 to 5, and X is an anion. Not more than one of $R_2$, $R_3$ or $R_4$ should be benzyl.

The preferred alkyl chain length for $R_1$ is $C_{12}-C_{15}$, particularly where the alkyl group is a mixture of chain lengths derived from coconut or palm kernel fat or is derived synthetically by olefin build up or OXO alcohols synthesis.

Preferred groups for $R_2R_3$ and $R_4$ are methyl and hydroxyethyl groups and the anion X may be selected from halide, methosulphate, acetate and phosphate ions.

Examples of suitable quaternary ammonium compounds of formulae (i) for use herein are:

coconut trimethyl ammonium chloride or bromide;

coconut methyl dihydroxyethyl ammonium chloride or bromide; decyl triethyl ammonium chloride;

decyl dimethyl hydroxyethyl ammonium chloride or bromide;

$C_{12-15}$ dimethyl hydroxyethyl ammonium chloride or bromide;

coconut dimethyl hydroxyethyl ammonium chloride or bromide;

myristyl trimethyl ammonium methyl sulphate;

lauryl dimethyl benzyl ammonium chloride or bromide;

lauryl dimethyl (ethenoxy)$_4$ ammonium chloride or bromide;

choline esters (compounds of formula (i) wherein $R_1$ is di-alkyl imidazolines [compounds of formula (i)].

Other cationic surfactants useful herein are also described in U.S. Pat. No. 4,228,044 and in EP 000 224.

When included therein, the laundry detergent compositions typically comprise from 0.2% to about 25%, preferably from about 1% to about 8% by weight of such cationic surfactants.

Ampholytic surfactants are also suitable for use in the laundry detergent. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. See U.S. Pat. No. 3,929,678 (column 19, lines 18–35) for examples of ampholytic surfactants.

When included therein, the laundry detergent compositions of the present invention typically comprise from 0.2% to about 15%, preferably from about 1% to about 10% by weight of such ampholytic surfactants.

Zwitterionic surfactants are also suitable for use in laundry detergent compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 (column 19, line 38 through column 22, line 48) for examples of zwitterionic surfactants.

When included therein, the laundry detergent compositions typically comprise from 0.2% to about 15%, preferably from about 1% to about 10% by weight of such zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula:

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3: and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

When included therein, the laundry detergent compositions typically comprise from 0.2% to about 15%, preferably from about 1% to about 10% by weight of such semi-polar nonionic surfactants.

Builder System

The compositions useful in the method of the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Another suitable inorganic builder material is layered silicate, e.g. SKS-6 (Hoechst). SKS-6 is a crystalline layered silicate consisting of sodium silicate ($Na_2Si_2O_5$).

Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenle-enschrift 2,446,686, and 2,446,487, U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2,-ethane tetracarboxylates, 1,1,3,3-propane tetracarboxylates containing sulfo substituents include the sulfosuccinate derivatives disclosed in British Patent Nos. 1,398, 421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis-cis-tetracarboxylates, cyclopentadienide pentacarboxylates, 2,3,4,5-tetrahydro-furan-cis,cis,cis-tetracarboxylates, 2,5-tetrahydro-furan-cis, discarboxylates, 2,2,5,5,-tetrahydrofuran-tetracarboxylates, 1,2,3,4,5,6-hexane-hexacarboxylates and carboxymethyl derivatives of polyhydric alcohols such as sorbitol, mannitol and xylitol. Aromatic polycarboxylates include mellitic acid, pyromellitic acid and the phthalic acid derivatives disclosed in British Patent No. 1,425,343.

Of the above, the preferred polycarboxylates are hydroxycarboxylates containing up to three carboxy groups per molecule, more particularly citrates.

Preferred builder systems for use in the compositions include a mixture of a water-insoluble aluminosilicate builder such as zeolite A or of a layered silicate (SKS-6), and a water-soluble carboxylate chelating agent such as citric acid.

A suitable chelant for inclusion in the detergent compositions is ethylenediamine-N,N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof. Examples of such preferred sodium salts of EDDS include $Na_2EDDS$ and $Na_4EDDS$. Examples of such preferred magnesium salts of EDDS include MgEDDS and $Mg_2EDDS$. The magnesium salts are the most preferred for inclusion in compositions in accordance with the invention.

Preferred builder systems include a mixture of a water-insoluble aluminosilicate builder such as zeolite A, and a water soluble carboxylate chelating agent such as citric acid.

Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated form each other by not more than two carbon atoms.

Polymers of this type are disclosed in G2-A-1,596,756. Examples of such salts are polyacrylates of MW 2000-5000 and their copolymers with maleic anhydride, such copolymers having a molecular weight of from 20,000 to 70,000, especially about 40,000.

Detergency builder salts are normally included in amounts of from 5% to 80% by weight of the composition. Preferred levels of builder for liquid detergents are from 5% to 30%.

Enzymes

Preferred detergent compositions useful in the method of the invention may advantageously comprise one or more enzymes which provides cleaning performance and/or fabric care benefits.

Such enzymes include proteases, lipases, cutinases, amylases, cellulases, peroxidases, oxidases (e.g. laccases).

Proteases:

Any protease suitable for use in alkaline solutions can be used. Suitable proteases include those of animal, vegetable or microbial origin. Microbial origin is preferred. Chemically or genetically modified mutants are included. The protease may be a serene protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270.

Preferred commercially available protease enzymes include those sold under the trade names Alcalase, Savinase, Primase, Durazyrm, and Esperase by Novo Nordisk A/S (Denmark), those sold under the tradename Maxatase, Maxacal, Maxapem, Properase, Purafect and Purafect OXP by Genencor International, and those sold under the tradename Opticlean and Optimase by Solvay Enzymes. Protease enzymes may be incorporated into the compositions in accordance with the invention at a level of from 0.00001% to 2% of enzyme protein by weight of the composition, preferably at a level of from 0.0001% to 1% of enzyme protein by weight of the composition, more preferably at a level of from 0.002% to 0.5% of enzyme protein by weight of the composition, even more preferably at a level of from 0.01% to 0.2% of enzyme protein by weight of the composition.

Lipases:

Any lipase suitable for use in alkaline solutions can be used. Suitable lipases include those of bacterial or fungal origin. Chemically or genetically modified mutants are included.

Examples of useful lipases include a *Humicola lanuginosa* lipase, e.g., as described in EP 258 068 and EP 305 216, a *Rhizomucor miehei* lipase, e.g., as described in EP 238 023, a Candida lipase, such as a *C. antarctica* lipase, e.g., the *C. antarctica* lipase A or B described in EP 214 761, a *Pseudomonas* lipase such as a *P. alcaligenes* and *P. pseudoalcaligenes* lipase, e.g., as described in EP 218 272, a *P. cepacia* lipase, e.g., as described in EP 331 376, a P. stutzeri lipase, e.g., as disclosed in GB 1,372,034, a P. fluorescens lipase, a Bacillus lipase, e.g., a *B. subtilis* lipase (Dartois et al., (1993), Biochemica et Biophysica acta 1131, 253–260), a *B. stearothermophilus* lipase (JP 64/744992) and a *B. pumilus* lipase (WO 91/16422).

Furthermore, a number of cloned lipases may be useful, including the *Penicillium camembertii* lipase described by Yamaguchi et al., (1991), Gene 103, 61–67), the *Geotricum candidum* lipase (Schimada, Y. et al., (1989), J. Biochem., 106, 383–388), and various Rhizopus lipases such as a *R. delemar* lipase (Hass, M. J et al., (1991), Gene 109, 117–113), a *R. niveus* lipase (Kugimiya et al., (1992), Biosci. Biotech. Biochem. 56, 716–719) and a *R. oryzae* lipase.

Other types of lipolytic enzymes such as cutinases may also be useful, e.g., a cutinase derived from *Pseudomonas mendocina* as described in WO 88/09367, or a cutinase derived from *Fusarium solani pisi* (e.g. described in WO 90/09446).

Especially suitable lipases are lipases such as Ml Lipase™, Luma fasts™ and Lipomax™ (Genencor), Lipolase™ and Lipolase Ultra™ (Novo Nordisk A/S), and Lipase P "Amano" (Amano Pharmaceutical Co. Ltd.).

The lipases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Amylases:

Any amylase (α and/or β) suitable for use in alkaline solutions can be used. Suitable amylases include those of bacterial or fungal origin. Chemically or genetically modified mutants are included. Amylases include, for example, α-amylases obtained from a special strain of *B. licheniformis*, described in more detail in GB 1,296,839. Commercially available amylases are Duramyl™, Termamyl™, Fungamyl™ and BAN™ (available from Novo Nordisk A/S) and Rapidase™ and Maxamyl P™ (available from Genencor).

The amylases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Cellulases:

Any cellulase suitable for use in alkaline solutions can be used. Suitable cellulases include those of bacterial or fungal origin. Chemically or genetically modified mutants are included. Suitable cellulases are disclosed in U.S. Pat. No. 4,435,307, which discloses fungal cellulases produced from *Humicola insolens*. Especially suitable cellulases are the cellulases having colour care benefits. Examples of such cellulases are cellulases described in European patent application No. 0 495 257.

Commercially available cellulases include Celluzyme™ produced by a strain of *Humicola insolens*, (Novo Nordisk A/S), is and KAC-500(B)™ (Kao Corporation).

Cellulases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Peroxidases/Oxidases:

Peroxidase enzymes are used in combination with hydrogen peroxide or a source thereof (e.g. a percarbonate, perborate or persulfate). Oxidase enzymes are used in combination with oxygen. Both types of enzymes are used for "solution bleaching", i.e. to prevent transfer of a textile dye from a dyed fabric to another fabric when said fabrics are washed together in a wash liquor, preferably together with an enhancing agent as described in e.g. WO 94/12621 and WO 95/01426. Suitable peroxidases/oxidases include those of plant, bacterial or fungal origin. Chemically or genetically modified mutants are included.

Peroxidase and/or oxidase enzymes are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Mixtures of the above mentioned enzymes are encompassed herein, in particular a mixture of a protease, an amylase, a lipase and/or a cellulase.

Any enzyme incorporated in the detergent composition is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

Bleaching agents:

Additional optional detergent ingredients that can be included in the detergent compositions useful in the method of the present invention include bleaching agents such as PB1, PB4 and percarbonate with a particle size of 400–800 microns. These bleaching agent components can include one or more oxygen bleaching agents and, depending upon the bleaching agent chosen, one or more bleach activators.

When present oxygen bleaching compounds will typically be present at levels of from about 1% to about 25%. In general, bleaching compounds are optional added components in non-liquid formulations, e.g. granular detergents.

The bleaching agent component for use herein can be any of the bleaching agents useful for detergent compositions including oxygen bleaches as well as others known in the art.

The bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. No. 4,483,781, U.S. Pat. No. 740,446, EP 0 133 354 and U.S. Pat. No. 4,412,934. Highly preferred bleaching agents also include 6-nonylamino-6-oxoperoxycaproic acid as described in U.S. Pat. No. 4,634,551.

Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

The hydrogen peroxide releasing agents can be used in combination with bleach activators such as tetraacetylethylenedlamine (TAED), nonanoyloxybenzenesulfonate (NOBS, described in U.S. Pat. No. 4,412,934), 3,5-trimethyl-hexsanoloxybenzenesulfonate (ISONOBS, described in EP 120 591) or pentaacetylglucose (PAG), which are perhydrolyzed to form a peracid as the active bleaching species, leading to improved bleaching effect. In addition, very suitable are the bleach activators C8(6-octanamido-caproyl) oxybenzene-sulfonate, C9(6-nonanamido caproyl) oxybenzenesulfonate and C10 (6-decanamido caproyl) oxybenzenesulfonate or mixtures thereof. Also suitable activators are acylated citrate esters such as disclosed in European Patent Application No. 91870207.7.

Useful bleaching agents, including peroxyacids and bleaching systems comprising bleach activators and peroxygen bleaching compounds for use in cleaning compositions according to the invention are described in application U.S. Ser. No. 08/136,626.

The hydrogen peroxide may also be present by adding an enzymatic system (i.e. an enzyme and a substrate therefore) which is capable of generation of hydrogen peroxide at the beginning or during the washing and/or rinsing process. Such enzymatic systems are disclosed in European Patent Application EP 0 537 381.

Bleaching agents other than oxygen bleaching agents are also known in the art and can be utilized herein. One type of non-oxygen bleaching agent of particular interest includes photoactivated bleaching agents such as the sulfonated zinc and/or aluminium phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, detergent composition will contain about 0.025% to about 1.25%, by weight, of sulfonated zinc phthalocyanine.

Bleaching agents may also comprise a manganese catalyst. The manganese catalyst may, e.g., be one of the compounds described in "Efficient manganese catalysts for low-temperature bleaching", Nature 369, 1994, pp. 637–639.

Suds Suppressors:

Another optional ingredient is a suds suppressor, exemplified by silicones, and silica-silicone mixtures. Silicones can generally be represented by alkylated polysiloxane materials, while silica is normally used in finely divided forms exemplified by silica aerogels and xerogels and hydrophobic silicas of various types. Theses materials can be incorporated as particulates, in which the suds suppressor is advantageously releasably incorporated in a water-soluble or waterdispersible, substantially non surface-active detergent impermeable carrier. Alternatively the suds suppressor can be dissolved or dispersed in a liquid carrier and applied by spraying on to one or more of the other components.

A preferred silicone suds controlling agent is disclosed in U.S. Pat. No. 3,933,672. Other particularly useful suds suppressors are the self-emulsifying silicone suds suppressors, described in German Patent Application DTOS 2,646,126. An example of such a compound is DC-544, commercially available form Dow Corning, which is a siloxane-glycol copolymer. Especially preferred suds controlling agent are the suds suppressor system comprising a mixture of silicone oils and 2-alkyl-alkanols. Suitable 2-alkyl-alkanols are 2-butyl-octanol which are commercially available under the trade name Isofl 12 R.

Such suds suppressor system are described in European Patent Application EP 0 593 841.

Especially preferred silicone suds controlling agents are described in European Patent Application No. 92201649.8. Said compositions can comprise a silicone/silica mixture in combination with fumed nonporous silica such as Aerosil$^R$.

The suds suppressors described above are normally employed at levels of from 0.001% to 2% by weight of the composition, preferably from 0.01% to 1% by weight.

Other components:

Other components used in detergent compositions may be employed such as soil-suspending agents, soil-releasing agents, optical brighteners, abrasives, bactericides, tarnish inhibitors, coloring agents, and/or encapsulated or nonencapsulated perfumes.

Especially suitable encapsulating materials are water soluble capsules which consist of a matrix of polysaccharide and polyhydroxy compounds such as described in GB 1,464,616.

Other suitable water soluble encapsulating materials comprise dextrins derived from ungelatinized starch acid esters of substituted dicarboxylic acids such as described in U.S. Pat. No. 3,455,838. These acid-ester dextrins are, preferably, prepared from such starches as waxy maize, waxy sorghum, sago, tapioca and potato. Suitable examples of said encapsulation materials include N-Lok manufactured by National Starch. The N-Lok encapsulating material consists of a modified maize starch and glucose. The starch is modified by adding monofunctional substituted groups such as octenyl succinic acid anhydride.

Antiredeposition and soil suspension agents suitable herein include cellulose derivatives such as methylcellulose, carboxymethylcellulose and hydroxyethylcellulose, and homo- or co-polymeric polycarboxylic acids or their salts. Polymers of this type include the polyacrylates and maleic anhydride-acrylic acid copolymers previously mentioned as builders, as well as copolymers of maleic anhydride with ethylene, methylvinyl ether or methacrylic acid, the maleic anhydride constituting at least 20 mole percent of the copolymer. These materials are normally used at levels of from 0.5% to 10% by weight, more preferably form 0.75% to 8%, most preferably from 1% to 6% by weight of the composition.

Preferred optical brighteners are anionic in character, examples of which are disodium 4,4'-bis-(2-diethanolamino-4-aniline-s-triazin-6-ylamino)stilbene-2:2' disulphonate, disodium 4,-4'-bis-(2-morpholino-4-anilino-s-triazin-6-ylamino-stilbene-2:2'-disuiphonate, disodium 4,4'-bis-(2,4-dianilino-s-triazin-6-ylamino)stilbene-2:2'-disulphonate, monosodium 4',4''-bis-(2,4-dianilino-s-tri-azin-6ylamino) stilbene-2-sulphonate, disodium 4,4'-bis-(2-anilino-4-(N-methyl-N-2-hydroxyethylamino)-s-triazin-6-ylamino) stilbene-2,2'-disulphonate, di-sodium 4,4'-bis-(4-phenyl-2, 1,3-triazol-2-yl)-stilbene-2,2' disulphonate, di-so-dium 4,4'bis(2-anilino-4-(1-methyl-2-hydroxyethylamino)-s-triazin-6-ylami-no)stilbene-2,2'disulphonate, sodium 2(stilbyl-4"-(naphtho-1',2':4,5)-1,2,3,-triazole-2"-sulphonate and 4,4'-bis(2-sulphostyryl)biphenyl.

Other useful polymeric materials are the polyethylene glycols, particularly those of molecular weight 1000–10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions used in the method of the present invention are conventionally copolymers or terpolymers of terephthalic acid with ethylene glycol and/or propylene glycol units in various arrangements. Examples of such polymers are disclosed in U.S. Pat. Nos. 4,116,885 and 4,711,730 and EP 0 272 033. A particular preferred polymer in accordance with EP 0 272 033 has the formula:

$(CH_3(PEG)_{43})_{0.75}(POH)_{0.25}[T-PO)_{2.8}(T-PEG)_{0.4}]$
$T(POH)_{0.25}((PEG)_{43}CH_3)_{0.75}$ where PEG is $-(OC_2H_4)O-$, PO is $(OC_3H_6O)$ and T is $(pOOC6H_4CO)$.

Also very useful are modified polyesters as random copolymers of dimethyl terephthalate, dimethyl sulfoisophthalate, ethylene glycol and 1,2-propanediol, the end groups consisting primarily of sulphobenzoate and secondarily of mono esters of ethylene glycol and/or 1,2-propanediol. The target is to obtain a polymer capped at both end by sulphobenzoate groups, "primarily", in the present context most of said copolymers herein will be endcapped by sulphobenzoate groups. However, some copolymers will be less than fully capped, and therefore their end groups may consist of monoester of ethylene glycol and/or 1,2-propanediol, thereof consist "secondarily" of such species.

The selected polyesters herein contain about 46% by weight of dimethyl terephthalic acid, about 16% by weight of 1,2-propanediol, about 10% by weight ethylene glycol, about 13% by weight of dimethyl sulfobenzoic acid and about 15% by weight of sulfoisophthalic acid, and have a molecular weight of about 3.000. The polyesters and their method of preparation are described in detail in EP 311 342.

Softening Agents:

Fabric softening agents can also be incorporated into laundry detergent compositions useful in accordance with the present invention. These agents may be inorganic or organic in type. Inorganic softening agents are exemplified by the smectite clays disclosed in GB-A-1 400898 and in U.S. Pat. No. 5,019,292. Organic fabric softening agents include the water insoluble tertiary amines as disclosed in GB-A1 514 276 and EP 0 011 340 and their combination with mono $C_{12}$–$C_{14}$ quaternary ammonium salts are disclosed in EP-B-0 026 528 and di-long-chain amides as disclosed in EP 0 242 919. Other useful organic ingredients of fabric softening systems include high molecular weight polyethylene oxide materials as disclosed in EP 0 299 575 and 0 313 146.

Levels of smectite clay are normally in the range from 5% to 15%, more preferably from 8% to 12% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

Polymeric Dye-Transfer Inhibiting Agents:

The detergent compositions may also comprise from 0.001% to 10%, preferably from 0.01% to 2%, more preferably form 0.05% to 1% by weight of polymeric dye-transfer inhibiting agents. Said polymeric dye-transfer inhibiting agents are normally incorporated into detergent compositions in order to inhibit the transfer of dyes from colored fabrics onto fabrics washed therewith. These polymers have the ability of complexing or adsorbing the fugitive dyes washed out of dyed fabrics before the dyes have the opportunity to become attached to other articles in the wash.

Especially suitable polymeric dye-transfer inhibiting agents are polyamine N-oxide polymers, copolymers of N-vinyl-pyrrolidone and N-vinylimidazole, polyvinylpyrrolidone polymers, polyvinyloxazolidones and polyvinylimidazoles or mixtures thereof.

Addition of such polymers also enhances the performance of the enzymes according the invention.

The detergent composition according to the invention can be in liquid, paste, gels, bars or granular forms.

Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

Granular compositions can also be in "compact form", i.e. they may have a relatively higher density than conventional granular detergents, i.e. form 550 to 950 g/l; in such case, the granular detergent compositions will contain a lower amount of "Inorganic filler salt", compared to conventional granular detergents; typical filler salts are alkaline earth metal salts of sulphates and chlorides, typically sodium sulphate; "Compact" detergent typically comprise not more than 10% filler salt. The liquid compositions can also be in "concentrated form", in such case, the liquid detergent compositions will contain a lower amount of water, compared to conventional liquid detergents. Typically, the water content of the concentrated liquid detergent is less than 30%, more preferably less than 20%, most preferably less than 10% by weight of the detergent compositions.

The compositions may for example be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

The following examples are meant to exemplify compositions useful in the method of the present invention, but are not necessarily meant to limit or otherwise define the scope of the invention.

In the detergent compositions, the abbreviated component identifications have the following meanings:
LAS: Sodium linear $C_{12}$ alkyl benzene sulphonate
TAS: Sodium tallow alkyl sulphate
XYAS: Sodium $C_{1X}$–$C_{1Y}$ alkyl sulfate
SS: Secondary soap surfactant of formula 2-butyl octanoic acid
25EY: A $C_{12}$–$C_{15}$ predominantly linear primary alcohol condensed with an average of Y moles of ethylene oxide
45EY: A $C_{14}$–$C_{15}$ predominantly linear primary alcohol condensed with an average of Y moles of ethylene oxide
XYEZS: $C_{1X}$–$C_{1Y}$ sodium alkyl sulfate condensed with an average of Z moles of ethylene oxide per mole
Nonionic: $C_{13}$–$C_{15}$ mixed ethoxylated/propoxylated fatty alcohol with an average degree of ethoxylation of 3.8 and an average degree of propoxylation of 4.5 sold under the tradename Plurafax LF404 by BASF GmbH
CFAA: $C_{12}$–$C_{14}$ alkyl N-methyl glucamide
TFAA: $C_{16}$–$C_{18}$ alkyl N-methyl glucamide
Silicate: Amorphous Sodium Silicate ($SiO_2$:$Na_2O$ ratio=2.0)
NaSKS-6: Crystalline layered silicate of formula δ-$Na_2Si_2O_5$
Carbonate: Anhydrous sodium carbonate
Phosphate: Sodium tripolyphosphate
MA/AA: Copolymer of 1:4 maleic/acrylic acid, average molecular weight about 80,000
Polyacrylate: Polyacrylate homopolymer with an average molecular weight of 8,000 sold under the tradename PA30 by BASF Gmbh
Zeolite A: Hydrated Sodium Aluminosilicate of formula $Na_{12}(AlO_2SiO_2)_{12}\cdot 27H_2O$ having a primary particle size in the range from 1 to 10 micrometers
Citrate: Tri-sodium citrate dihydrate
Citric: Citric Acid
Perborate: Anhydrous sodium perborate monohydrate bleach, empirical formula $NaBO_2.H_2O_2$
PB4: Anhydrous sodium perborate tetrahydrate
Percarbonate: Anhydrous sodium percarbonate bleach of empirical formula $2Na_2CO_3.3H_2O_2$
TAED: Tetraacetyl ethylene diamine
CMC: Sodium carboxymethyl cellulose
DETPMP: Diethylene triamine penta (methylene phosphonic acid), marketed by Monsanto under the Tradename Dequest 2060
PVP: Polyvinylpyrrolidone polymer
EDDS: Ethylenediamine-N,N'-disuccinic acid, [S,S] isomer in the form of the sodium salt
Suds 25% paraffin wax Mpt 50° C., 17% hydrophobic silica, 58% suppressor paraffin oil
Granular Suds 12% Silicone/silica, 18% stearyl alcohol, 70% suppressor starch in granular form
Sulphate: Anhydrous sodium sulphate
HMWPEO: High molecular weight polyethylene oxide
TAE 25: Tallow alcohol ethoxylate (25)

DETERGENT EXAMPLE I

A granular fabric cleaning composition in accordance with the invention may be prepared as follows:

| | |
|---|---|
| Sodium linear $C_{12}$ alkyl benzene sulfonate | 6.5 |
| Sodium sulfate | 15.0 |
| Zeolite A | 26.0 |
| Sodium nitrilotriacetate | 5.0 |
| Enzyme of the invention | 0.1 |
| PVP | 0.5 |
| TAED | 3.0 |
| Boric acid | 4.0 |
| Perborate | 18.0 |
| Phenol sulphonate | 0.1 |
| Minors | Up to 100 |

DETERGENT EXAMPLE II

A compact granular fabric cleaning composition (density 800 g/l) in accord with the invention may be prepared as follows:

| | |
|---|---|
| 45AS | 8.0 |
| 25E3S | 2.0 |
| 25E5 | 3.0 |
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |
| CMC | 0.4 |
| Enzyme of the invention | 0.1 |
| TAED | 6.0 |
| Percarbonate | 22.0 |
| EDDS | 0.3 |
| Granular suds suppressor | 3.5 |
| water/minors | Up to 100 |

DETERGENT EXAMPLE III

Granular fabric cleaning compositions in accordance with the invention which are especially useful in the laundering of coloured fabrics were prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |
| 25E5 | — | 8.0 |
| Citrate | 15.0 | 7.0 |
| Carbonate | — | 10 |
| Citric acid | 2.5 | 3.0 |
| Zeolite A | 32.1 | 25.0 |
| Na-SS-6 | — | 9.0 |

-continued

|  |  |  |
|---|---|---|
| MA/AA | 5.0 | 5.0 |
| DETPNP | 0.2 | 0.8 |
| Enzyme of the invention | 0.10 | 0.05 |
| Silicate | 2.5 | — |
| Sulphate | 5.2 | 3.0 |
| PVP | 0.5 | — |
| Poly (4-vinylpyridine)-N-Oxide/copolymer of vinyl-imidazole and vinyl-pyrrolidone | — | 0.2 |
| Perborate | 10 | — |
| Phenol sulfonate | 0.2 | — |
| Water/Minors | Up to 100% | |

DETERGENT EXAMPLE IV

Granular fabric cleaning compositions in accordance with the invention which provide "Softening through the wash" capability may be prepared as follows:

|  |  |  |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Enzyme of the invention | 0.10 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | Up to 100% | |

DETERGENT EXAMPLE V

Heavy duty liquid fabric cleaning compositions in accordance with the invention may be prepared as follows:

|  | I | II |
|---|---|---|
| LAS acid form | — | 25.0 |
| Citric acid | 5.0 | 2.0 |
| 25A5 acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | — |
| Enzyme of the invention | 0.10 | 0.05 |
| Coco-alkyl dimethyl hydroxy ethyl ammonium chloride | — | 3.0 |
| Smectite clay | — | 5.0 |

-continued

|  | I | II |
|---|---|---|
| PVP | 2.0 | — |
| Water / Minors | Up to 100% | |

In a preferred embodiment, the detergent or cleaning composition comprises the cationic polymer in an amount effective for killing or inhibiting cells, preferably in an amount above 1 ppm, more preferably above 10 ppm.

When used for preservation of cosmetics such as lotions, creams, gels, ointments, soaps, shampoos, conditioners, antiperspirants, mouth wash; contact lens products, enzyme formulations, the composition used in the method of the present invention may be incorporated into the unpreserved cosmetics, contact lens products or antiinflammatory product in an amount effective for killing or inhibiting growing microbial cells.

Thus, the composition used in the method of the invention may by useful as a disinfectant, e.g in the treatment of acne, infections in the eye or the mouth, skin infections; in antiperspirants; for cleaning end disinfection of contact lenses, hard surfaces, wounds, bruises and the like.

Preferably, the method of the invention is carried out at a relatively high pH, since it is contemplated that the bacteriocidal activities are optimal at high pH values. However, the pH has to be below the pI of the cationic polymers to obtain maxmium bacteriocidal activity.

The invention is illustrated by the following non-limiting examples.

EXAMPLE 1

Indirect Malthus measurements were used when measuring antibacterial activity (Malthus Flexi M2060, Malthus Instrument Limited). 3 ml of Tryptone Soya Broth (TSB) were transferred to the outer chamber of the indirect Malthus cells, and 0.5 ml of sterile KOH (0.1 M) were transferred to the inner chamber. Cationic polymers were added to the TSB in increasing concentrations and the substrate was innoculated with approximately $10^3$ cfu/ml and incubated in the Malthus incubator. As cells are growing in the outer chamber they produce $CO_2$ which will dissolve in the KOH in the inner chamber and thereby change the conductance of the KOH. When the conductance change is measurable by the Malthus, a detection time (dt) will be recorded. If the cells are inhibited by the cationic polymers the detection time will be prolonged or absent.

For determination of a bacteriocidal activity a series 10-fold dilution rate was prepared from a $10^8$ cfu/ml suspension of cells. Conductance dt of each dilution step was determined in for each test organism, and a calibration curve relating cfu/ml of the 10 fold dilutions to dt in TSB was constructed for each strain.

A cell suspension with approximately $10^4$ cfu/ml were treated with increasing concentrations of polymer, from the polymer treated suspensions, 0.1 ml was inoculated in TSB in Malthus cells and the dt determined. This dt was, converted to a colony count using the calibration curve. Thus, colony counts were not made directly on the polymer treated suspensions as protamine caused significant clumping of the bacterial cells. When no dt was measured, 0.1 ml from the Malthus cell was pipetted onto agar plates.

Bacteristatic activity is measured as growth inhibition for 100 hours, and Minimum Inhibitory Concentration (MIC) is determined as the lowest concentration of polymer inhibiting the cells for 100 hours.

Bacteriocidal activity is measured as a total kill after 30 min when the cells are in a non-growing state. Minimum Bacteriocidal Concentration (MBC) is determined as the lowest concentration of polymer causing a 100° o kill of the test organisms.
The following polymers were tested:
A: Polyvinylamine, K-value 30
B: Copolymer (70 mol % vinylamine/30 mol % vinvlalcohol), K-value 49
C: Copolymer (vinylamine/vinylformate)
D: Copolymer (80 mol % vinylamine/20 mol % vinylurea), K-value 80.

Test of polymer "A":

| Test organism | MIC (mg/ml) |
|---|---|
| Gram-positive | |
| Bacillus subtilis | 500 |
| Listeria monocytogenes | 1000 |
| Staphylococcus aureus | 500 |
| Streptococcus mutans | 500 |
| Gram-negative | |
| Escherichia coli | 4000 |
| Pseudomonas aeruginosa | 4000 |
| Pseudomonas fluorescens | 2000 |
| Shewanella putrefaciens | 1000 |
| Vibrio parahaemolyticus | 1000 |

Test of growth inhibition:

| Test organism | MIC, (mg/ml) | | | |
|---|---|---|---|---|
| | A | B | C | D |
| Gram-positive | | | | |
| Bacillus subtilis | 100 | 500 | 100 | 100 |
| Staphylococcus aureus | 500 | 500 | 100 | 500 |
| Gram-negative | | | | |
| Pseudomonas fluorescens | 2000 | n.e. | n.e. | 2000 |
| Shewanella putrefaciens | 1000 | >2000 | n.e. | 2000 | n.e. not effective

Test of 100% Disinfection

| Test organism | Minimum Bactericidal Concentration, MBC (mg/ml) | | | |
|---|---|---|---|---|
| | A | B | C | D |
| Staphylococcus aureus | 100 | 100 | 100 | 100 |
| Streptococcus mutans | 500 | n.e. | 2000 | 2000 |
| Pseudomonas fluorescens | >2000 | n.e. | 500 | 2000 |
| Shewanella putrefaciens | >2000 | n.e. | 500 | >2000 | n.e. not effective

EXAMPLE 2

Synergistic effects were determined by a multi factorial experiment with Staphylococcus epidermidis DSM 20 042 as test organism.

Staphylococcus epidermidis was grown in BHI at 30° C. for 24 hours. The cells were diluted to approximately $10^6$ cfu/ml in phosphate buffer (pH 7.0) containing glucose (3 g/L). Polyvinyl amine (A) was added to the final concentration of 250 µg/ml, lysozyme (Serva 28262, lot 12072C) 20.000 U/ml and glucose oxidase (Sigma G7019) 1 U/ml were added and after 15 minutes at 20° C. 0.1 ml was inoculated to Malthus tubes containing BHI. The Malthus tubes were incubated in Malthus at 30° C. until detection. The bacteriocidal activity was determined as described in example 1.

Figure 1:
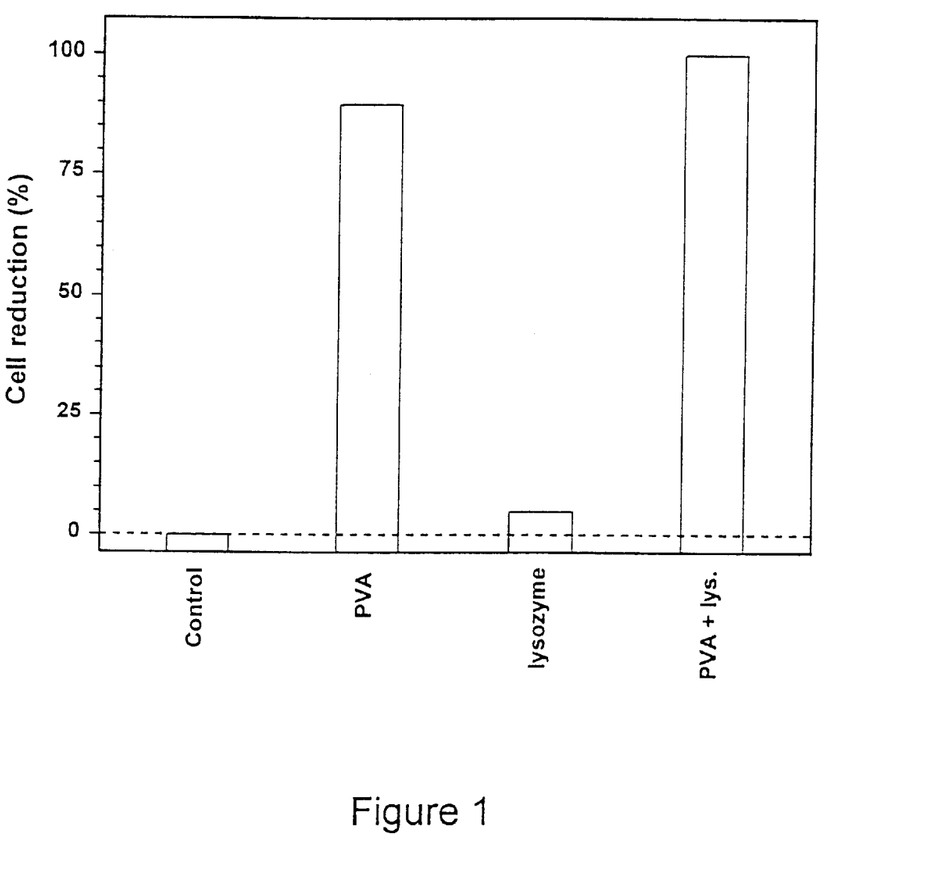
Figure 2:
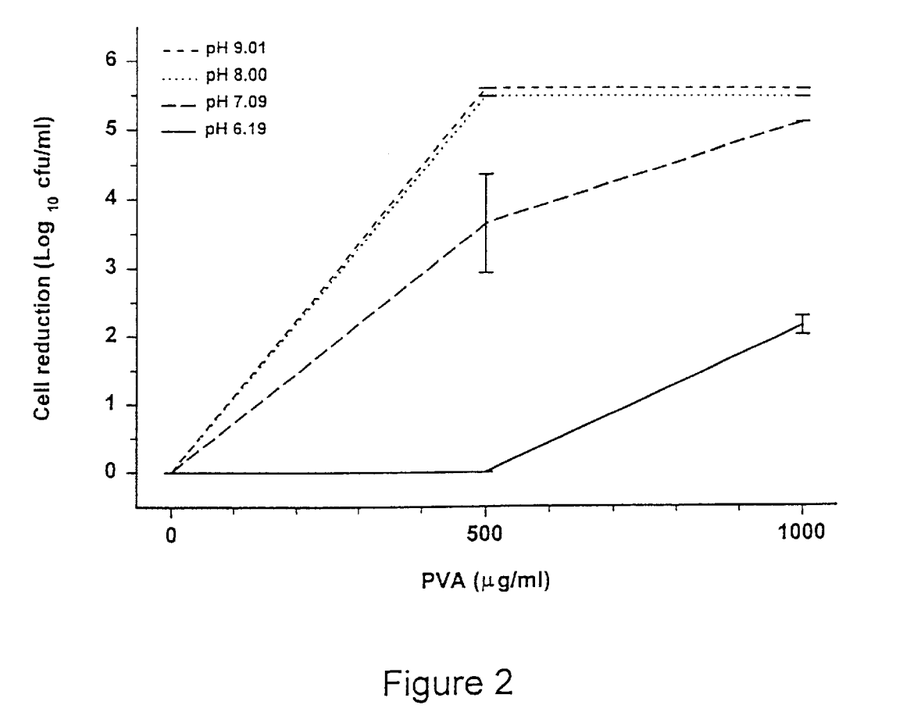

A synergistic effect between PVA and enzyme was observed (FIG. 1) as the concentration of PVA needed for a total inhibition of the test organism was reduced to 250 µg/ml when lysozyme was present. Without lysozyme, 1000 µg/ml of PVA was necessary for a 100% cell reduction at pH 7 (FIG. 2 and example 2).

EXAMPLE 3

The bacteriocidal activity against Staphylococcus epidermidis DSM 20 042 at different pH values was determined by use of direct Malthus measurements.

Staphylococcus epidermidis were grown in Brain Heart Infusion Broth (BHI) (Oxoid CM225) at 30° C. for 24 hours. Cells were diluted to approximately $10^6$ cfu/ml in buffers with pH 6.19, 7.09, 8.00 or 9.01. The physiological buffer solutions were made with a constant ionic strength (I=0.05) after Miller & Golder (Miller & Golder, Arch. Biochem. 29, 420 (1950)).

Polyvinyl amine (A) was added to the cell suspensions to a final concentration of 0, 500 or 1000 µg/ml. After 30 minutes at 20° C., 0.1 ml of the cell suspension were inoculated to Malthus cells containing BHI and incubated in Malthus until detection.

The bacteriocidal activity of PVA was increased at high pH values (FIG. 2). No cells were killed with 500 µg/ml at pH 6 and increasing the concentration to 1000 µg/ml caused a cell reduction of approximately 2 log-units. Whereas at pH 8 or 9 a total kill was observed with 500 µg/ml.

REFERENCES

Christensen, B., Fink, J., Merrifield, R. B. & Mauzerall, D. 1988 Channel-forming properties of cecropins and related model compounds incorporated into planar lipid membranes. Proceedings of the National Academy of Sciences of the United States of America 85, 5072–5076.

Farrag, S. A. & Marth, E. H. 1992 Escherichia coli O157: H7, Yersinia enterocolitica and their control in milk by the lactoperoxidase system: a review. Lebensmittel-Wissenschaft und Technologie 25, 201–211.

Hugo, W. B. 1978 Membrane-active antimicrobial drugs—a reappraisal of their mode of action in the light of the chemosmotic theory. International Journal of Pharmaceutics 1, 127–131.

Islam, N. MD., Itakura, T. & Motohiro, T. 1984 Antibacterial spectra and minimum inhibition concentration of clupeine and salmine. Bulletin of the Japanese Society of Scientific Fisheries 50, 1705–1708.

Jeong, D. K., Harrison, M. A., Frank, J. F. & Wicker, L. 1992 Trials on the antibacterial effect of glucose oxidase on chicken breast skin and muscle. Journal of Food safety 13, 43–49.

Jeppesen, V. F. & Huss, H. H. 1993 Characteristics and antagonistic activity of lactic acid bacteria isolated from chilled fish products. International Journal of Food Microbiology 18, 305–320.

Johansen, C., Gram, L. & Meyer, A. S. 1994 The combined inhibitory effect of lysozyme and low pH on the growth of Listeria monocytogenes. Journal of Food Protection, in press.

Kagan, B. L., Selsted, m. E., Ganz, T. & Lehrer, R. I. 1990 Antimicrobial defensin peptides from voltage-dependent ion-permeable channels in planar lipid bilayer membranes. *Proceedings of the National Academy of Sciences of the United States of America* 87, 210–214.

Nakae, T. 1985 Outer-membrane permeability of bacteria. In *Critical Reviews in Microbiology* ed. O'Leary, W. M., pp. 1–62. Boca Raton, Fla.: CRC Press, Inc.

Trevors, J. T. 1986 Bacterial growth and activity as indicators of toxicity. In *Toxicity testing using microorganisms* ed. Bitton, G. & Dutka, B. J. Boca Raton, Fla.: CRC Press, Inc.

Vaara, M. 1992 Agents that increase the permeability of the outer membrane. *Microbiological Reviews* 56, 395–411.

Vaara, M. & Vaara, T. 1983 Polycations as outer membrane-disorganizing agents. *Antimicrobial Agents and Chemotherapy* 24, 114–122.

What is claimed is:

1. A method of inhibiting microorganisms present in laundry, said method comprising treating the laundry with a soaking, washing or rinsing liquor comprising a poly-cationic compound and one or more of an oxidase or a peroxidase, under conditions effective to inhibit said microorganisms, wherein the poly-cationic compound is a polymer comprising:
    a) 0.1 to 100 mol % vinyl amine or ethyleneimine units;
    b) 0 to 99.9 mol % units of at least one monomer selected from the group consisting of N-vinylcarboxamides of the formula I wherein $R^1$ and $R^2$ are hydrogen or $C_1$–$C_6$-alkyl; vinyl formate, vinyl acetate, vinyl propionate vinyl alcohol, $C_1$–$C_6$-alkyl vinyl ethers mono ethylenic unsaturated $C_3$–$C_8$-carboxylic acid, and esters, nitriles, amides and anhydrides thereof, N-vinylurea, N-imidazoles and N-vinyl imidazolines; and
    c) 0 to 5 mol % units of monomers having at least two unsaturated ethylenic double bonds, wherein the total amount of a), b) and c) in the polymer being 100 mol.

2. The method according to claim 1, wherein the peroxidase is a peroxidase enzyme system which comprises at least one peroxidase enzyme and a hydrogen peroxide generating enzyme system.

3. The method according to claim 1, wherein the poly-cationic compound is a polymer selected from the group consisting of polyamino acids, polyvinylamines, copolymers prepared from vinylamine and one or more carboxylic acid anhydrides, and water soluble salts thereof.

4. The method according to claim 1, wherein the polymer contains polymerized units of
    a) vinylamine, and
    b) N-vinylformamide, vinylformate, vinylacetate, vinylpropionate, vinylalcohol, and/or N-vinylurea.

5. A method of inhibiting microorganisms present in laundry, said method comprising treating the laundry with a soaking, washing or rinsing liquor comprising a poly-cationic compound and one or more of an oxidase or a peroxidase, under conditions effective to inhibit said microorganisms, wherein the poly-cationic compound is a polymer comprising:
    a) 1–99 mol % of vinylamine units, and
    b) 1–99 mol % of N-vinylformamide having a K-value from 5 to 300, wherein the total amount of a) and b), calculated in mol %, being 100.

6. The method according to claim 5, wherein the polymer comprises 10–90 mol % of N-vinylformamide having a K value from 5 to 300.

7. The method according to claim 5, wherein the polymer comprises 10–90 mol % of N-vinylformamide having a K value from 10–120.

8. The method according to claim 5, wherein the peroxidase is a peroxidase enzyme system which comprises at least one peroxidase and a hydrogen peroxide generating enzyme system.

* * * * *